United States Patent [19]

Stetter et al.

[11] 4,396,624
[45] Aug. 2, 1983

[54] COMBATING FUNGI WITH 1-(AZOL-1-YL)-2-HYDROXY-OR-KETO-1-PYRIDINYLOXY-ALKANES

[75] Inventors: Jörg Stetter, Wuppertal; Udo Kraatz, Leverkusen; Karl H. Büchel, Wuppertal; Paul-Ernst Frohberger, Leverkusen; Wilhelm Brandes, Leichlingen; Volker Paul, Solingen, all of Fed. Rep. of Germany

[73] Assignee: Bayer Aktiengesellschaft, Leverkusen, Fed. Rep. of Germany

[21] Appl. No.: 964,768

[22] Filed: Nov. 29, 1978

[30] Foreign Application Priority Data

Dec. 16, 1977 [DE] Fed. Rep. of Germany ....... 2756269

[51] Int. Cl.³ .................. C07D 401/12; A01N 43/40
[52] U.S. Cl. ........................................ 424/263; 546/2; 546/8; 546/9; 546/276; 546/278; 546/302; 548/262
[58] Field of Search .................. 546/276, 278, 2, 8, 546/9; 424/263; 548/262

[56] References Cited

U.S. PATENT DOCUMENTS 3,927,011 12/1975 Nakanishi et al. ............ 546/278 OR
4,005,083 1/1977 Heinz et al. ..................... 424/245
4,013,677 3/1977 Stolzer et al. .................... 260/308 R
4,107,314 8/1978 Cox et al. ......................... 424/263
4,166,854 9/1979 Carson et al. .................... 546/276 X

OTHER PUBLICATIONS

Burger, Medicinal Chemistry, Second Edition, pp. 79–81, Interscience Publishers, Inc. NY (1960).

*Primary Examiner*—Alan L. Rotman
*Attorney, Agent, or Firm*—Sprung, Horn, Kramer & Woods

[57] ABSTRACT

1-(Azol-1-yl)-2-hydroxy-or-keto-pyridinyloxy-alkanes of the formula

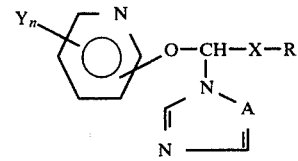

in which
A is CH or N,
R is alkyl
X is —CO— or —CH(OH)—
Y is halogen, alkyl, halogenoalkyl, alkenyl, alkynyl, alkoxy, alkylthio, nitro, cyano, optionally substituted aryl or optionally substituted aryloxy, and
n is 0, 1, 2 or 3, an acid addition salt thereof, or a metal salt complex thereof, which possess fungicidal properties.

3 Claims, No Drawings

COMBATING FUNGI WITH 1-(AZOL-1-YL)-2-HYDROXY-OR-KETO-1-PYRIDINYLOXY-ALKANES

The present invention relates to and has for its objects the provision of particular new 1-(azol-1-yl)-2-hydroxy-or-keto-pyridinyloxy-alkanes which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that trityl-imidazoles and -1,2,4-triazoles, such as 1-triphenylmethyl-imidazole and 1-triphenylmethyl-1,2,4-triazole, have a good fungicidal activity (see U.S. Pat. No. 3,321,366 and DT-OS (German Published Specification) No. 1,795,249). However, their action is not always completely satisfactory, especially when low amounts and concentrations are used.

The present invention provides the azolylalkyl pyridinyl ethers of the general formula

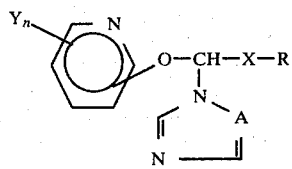

in which
A represents the CH group or a nitrogen atom,
R represents alkyl,
X represents a keto group or a CH(OH) grouping,
Y represents halogen, alkyl, halogenoalkyl, alkenyl, alkynyl, alkoxy, alkylthio, nitro, cyano or optionally substituted aryl or aryloxy and
n represents the number 0, 1, 2 or 3,
and acid addition salts thereof and metal salt complexes thereof. They have powerful fungicidal properties.

Preferaly, R represents straight-chain or branched alkyl with 1 to 4 carbon atoms, and Y represents fluorine, chlorine, bromine, iodine, straight-chain or branched alkyl with 1 to 4 carbon atoms, halogenoalkyl with up to 2 carbon atoms and up to 5 halogen atoms (especially with up to 3 identical or different halogen atoms, preferred halogens being fluorine and chlorine; an example which may be mentioned is trifluoromethyl), alkenyl or alkynyl with in either case 2 to 4 carbon atoms, alkoxy or alkylthio with in either case 1 to 4 carbon atoms, nitro, cyano or optionally substituted aryl or aryloxy with in either case 6 to 10 carbon atoms (especially phenyl, naphthyl, phenyloxy or naphthyloxy) preferred substituents of these radicals being halogen (especially fluorine, chlorine or bromine), alkyl, alkoxy or alkylthio with in each case 1 to 2 carbon atoms and halogenoalkyl with up to 2 carbon atoms and up to 3 identical or different halogen atoms (preferred halogens being fluorine and chlorine).

Those compounds of the formula (I) in which X represents the CH(OH) group possess two asymmetric carbon atoms; they can therefore exist in the form of the two geometric isomers (ervthro form and threo form), which can be obtained in various proportions. In both cases they exist in the form of optical isomers. The formula (I) embraces all the isomers.

Surprisingly, the active compounds according to the invention exhibit a considerably higher fungicidal activity, in particular against cereal diseases, than the compounds 1-triphenylmethyl-imidazole and 1-triphenylmethyl-1,2,4-triazole known from the state of the art, which are known substances of the same type of action. The active compounds according to the invention thus represent an enrichment of the art.

The present invention also provides a process for the preparation of an azolylalkyl pyridinyl ether of the formula (I) in which
(a) an azolylhalogenoketone of the general formula

in which
A and R have the meanings stated above and
Hal represents chlorine or bromine,
is reacted with a pyridinol of the general formula

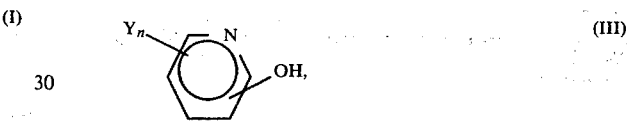

in which
Y and n have the meanings stated aove, in the presence of an acid-binding agent and optionally in the presence of a diluent, or
(b) a halogeno ether-ketone of the general formula

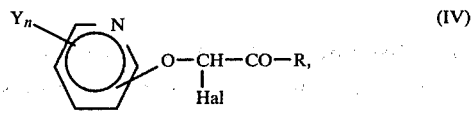

in which
Hal, R, Y and n have the meanings stated above, is reacted with imidazole or 1,2,4-triazole in the presence of an acid-binding agent and optionally in the presence of a diluent, or
(c) a dihalogenoketone of the general formula

$$(Hal)_2CH-CO-R \qquad (V)$$

in which
R and Hal have the meanings stated above, is reacted with imidazole or 1,2,4-triazole and with a pyridinol of the formula (III) in the presence of an acid-binding agent and optionally in the presence of a diluent, and the keto derivative obtained according to process variant (a), (b) or (c) is optionally reduced by known methods in the customary manner.

An acid or a metal salt can then optionally be added onto the compound of the formula (I) thus obtained.

If 1-bromo-3,3-dimethyl-1-(1,2,4-triazol-1-yl)-butan-2-one and 6-chloro-pyridin-2-ol are used as starting materials in process variant (a), the course of the reaction can be represented by the equation which follows:

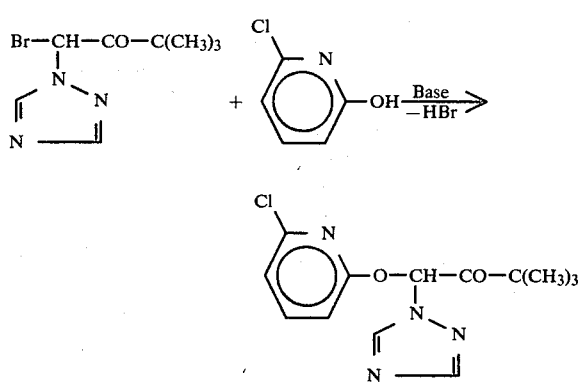

If 1-bromo-1-(6-chloro-pyridin-2-yl-oxy)-3,3-dimethylbutan-2-one and imidazole are used as starting materials in process variant (b), the course of the reaction can be represented by the equation which follows:

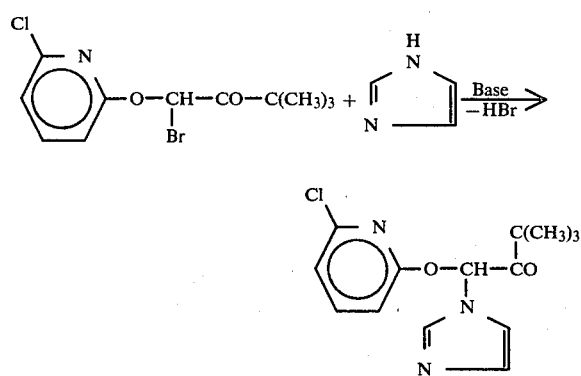

If 6-chloro-pyridin-2-ol, dichloropinacolin and 1,2,4-triazole are used as starting materials in process variant (c), the course of the reaction can be represented by the equation which follows:

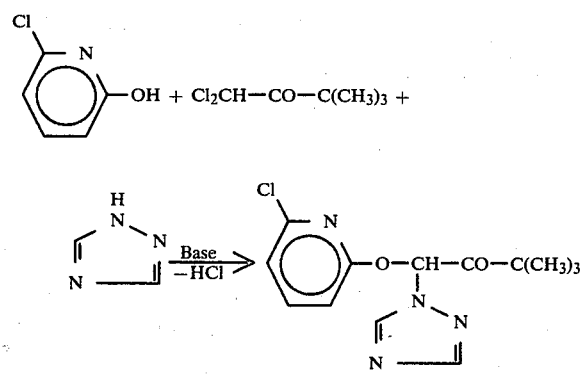

If 1-(6-chloro-pyridin-2-yl-oxy)-3,3-dimethyl-1-(1,2,4-triazol-1-yl)-butan-2-one is used as the ketone and sodium borohydride is used as the reducing agent, the course of the reduction reaction can be represented by the equation which follows:

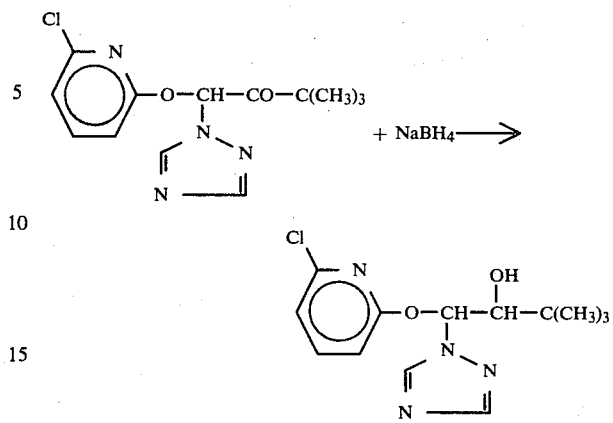

The azolylhalogenoketones of the formula (II) have not hitherto been described in the literature but they can be prepared by known processes by reacting known halides (see U.S. application Ser. No. 782,263, filed Mar. 25, 1977) of the general formula

with imidazole or 1,2,4-triazole in the presence of an acid-binding agent, such as, for example, potassium carbonate, and in the presence of an inert organic solvent, such as, for example, acetone, at temperatures between 60° and 120° C. One of the two active hydrogen atoms is then replaced by chlorine or bromine in the customary manner.

Examples which may be mentioned of the starting materials of the formula (II) are: 1-bromo-3,3-dimethyl-1-(1,2,4-triazol-1-yl)-butan-2-one, 1-chloro-3,3-dimethyl-1-(1,2,4-triazol-1-yl)-butan-2-one, 1-bromo-3,3-dimethyl-1-imidazol-1-yl-butan-2-one, 1-chloro-3,3-dimethyl-1-imidazol-1-yl-butan-2-one, 1-bromo-1-(1,2,4-triazol-1-yl)-propan-2-one, 1-bromo-1-imidazol-1-yl-propan-2-one, 1-bromo-3-methyl-1-(1,2,4-triazol-1-yl)-butan-2-one, 1-bromo-1-imidazol-1-yl-3-methyl-butan-2-one, 1-bromo-3,3-dimethyl-1-(1,2,4-triazol-1-yl)-pentan-2-one and 1-bromo-3,3-dimethyl-1-imidazol-1-yl-pentan-2-one.

The pyridinols of the formula (III) are generally known compounds of organic chemistry. Examples which may be mentioned are: 2-hydroxy-pyridine, 3-hydroxy-pyridine, 4-hydroxy-pyridine, 2-hydroxy-6-chloro-pyridine, 2-hydroxy-5-chloro-pyridine, 2-hydroxy-4-chloro-pyridine, 2-hydroxy-3-chloro-pyridine, 2-hydroxy-6-bromo-pyridine, 2-hydroxy-5-bromo-pyridine, 2-hydroxy-4-bromo-pyridine, 2-hydroxy-3-bromo-pyridine, 2-hydroxy-6-methyl-pyridine, 2-hydroxy-5-methyl-pyridine, 2-hydroxy-4-methyl-pyridine, 2-hydroxy-3-methyl-pyridine, 2-hydroxy-6-fluoro-pyridine, 2-hydroxy-5-fluoro-pyridine, 2-hydroxy-4-fluoro-pyridine, 2-hydroxy-3-fluoro-pyridine, 3-hydroxy-2-chloro-pyridine, 3-hydroxy-2-bromo-pyridine, 3-hydroxy-2-fluoro-pyridine, 3-hydroxy-2-iodo-pyridine, 3-hydroxy-2-methoxy-pyridine, 3-hydroxy-6-chloro-pyridine, 3-hydroxy-5-chloro-pyridine, 4-hydroxy-2-chloro-pyridine and 4-hydroxy-3-chloro-pyridine.

The halogeno ether-ketones of the formula (IV) have not yet been described in the literature, but they can be prepared by known processes by reacting pyridinols of the formula (III) with halogenoketones of the formula (VI) in the presence of an acid-binding agent, such as, for example, potassium carbonate, and in the presence of an inert organic solvent, such as, for example, acetone, at temperatures between 60° and 120° C. One of the two active hydrogen atoms is then replaced by chlorine or bromine in the customary manner.

Examples which may be mentioned of starting materials of the formula (IV) are: 1-bromo-3,3-dimethyl-1-pyridin-2-yl-butan-2one, 1-bromo-3,3-dimethyl-1-pyridin-3-yl-butan-2-one, 1-bromo-3,3-dimethyl-1-pyridin-4-yl-butan-2-one, 1-bromo-1-(6-chloro-pyridin-2-yl)-3,3-dimethyl-butan-2-one, 1-chloro-1-(6-chloro-pyridin-2-yl)-3,3-dimethyl-butan-2-one, 1-bromo-1-(5-chloro-pyridin-2-yl)-3,3-dimethyl-butan-2-one, 1-bromo-1-(2-chloro-pyridin-3-yl)-3,3-dimethyl-butan-2-one, 1-bromo-1-(2-bromo-pyridin-3-yl)-3,3-dimethyl-butan-2-one and 1-bromo-1-(3,4,5-trichloro-pyridin-2-yl)-3,3-dimethyl-butan-2-one.

The dihalogenoketones of the formula (V) are generally known compounds of organic chemistry. Examples which may be mentioned are: dichloropinacolin and dibromopinacolin.

Possible diluents for the reactions according to the invention of process variants (a) and (b) are inert organic solvents, especially ketones, such as diethyl ketone, and in particular acetone and methyl ethyl ketone; nitriles, such as propionitrile, and in particular acetonitrile; alcohols, such as ethanol or isopropanol; ethers, such as tetrahydrofuran or dioxane; benzene; formamides, such as, in particular, dimethylformamide; and halogenated hydrocarbons.

The reactions according to process variants (a) and (b) are carried out in the presence of an acid-binding agent. It is possible to add any of the inorganic or organic acid-binding agents which can usually be employed, such as alkali metal carbonates, for example sodium carbonate and potassium carbonate, and sodium bicarbonate, or such as lower tertiary alkylamines, cycloalkylamines and or aralkylamines, for example triethylamine and dimethylbenzylamine; or such as pyridine and diazabicyclooctane.

In the case of process variant (b), it is also possible to use an appropriate excess of azole.

The reaction temperatures in process variants (a) and (b) can be varied within a substantial range. In general, the processes are carried out at from 20° to 150° C., preferably at from 60° to 120° C. If a solvent is present, the processes are appropriately carried out at the boiling point of the particular solvent.

In carrying out process variants (a) and (b) according to the invention, 1 to 2 moles of the pyridinol of the formula (III) or, respectively, 1 to 2 moles of the azole and in each case 1 to 2 moles of acid-binding agent are preferably employed per mole of the compound of the formula (II) or (IV) respectively. In order to isolate the compound of the formula (I), the solvent is distilled off and either water is added to the residue and the mixture is stirred vigorously, whereupon the reaction product crystallizes completely, or the residue is taken up in a mixture of an organic solvent and water and the organic phase is separated off, washed with water, dried over sodium sulphate and freed from solvent in vacuo. The residue is appropriately purified by distillation or recrystallization.

Preferred diluents for the reaction according to the invention of process variant (c) are polar organic solvents, especially chlorinated hydrocarbons, such as dichloroethane; alcohols, such as ethanol, propanol and n-butanol; ketones; such as acetone, methyl ethyl ketone and methyl butyl ketones; ethers, such as tetrahydrofuran and dioxane; and nitriles, such as acetonitrile.

The reaction according to process variant (c) is carried out in the presence of an acid-binding agent. The preferred acid-binding agents include the inorganic and organic acid-binding agents which have already been mentioned as preferred in the case of process variants (a) and (b).

The reaction temperatures in process (c) can be varied within a substantial range. In general, the process is carried out at from 0° to 150° C., preferably from 50° to 90° C.

In carrying out process variant (c) according to the invention, 1 mole of pyridinol, 1 to 1.2 moles of azole and 2 to 3 moles of acid-binding agent are preferaly employed per mole of dihalogenoketone of the formula (V). In order to isolate the compound of the formula (I), the solvent is largely distilled off in vacuo. A little dilute hydrochloric acid is added to the residue in the presence of an inert water-immiscible solvent, such as, for example, toluene, xylene or dichloroethane, in order to remove excess azole as the hydrochloride. Thereafter, the organic phase is washed with dilute alkali metal hydroxide solution until neutral and the solvent is distilled off in vacuo. The residue is approximately purified by distillation or recrystallization.

The reduction according to the invention is carried out in the customary manner, such as, for example, by reaction with complex hydrides, optionally in the presence of a diluent, or by reaction with aluminum isopropylate in the presence of a diluent.

If complex hydrides are used, possible diluents for the reaction according to the invention are polar organic solvents, especially alcohols, such as methanol, ethanol, butanol and isopropanol, and ethers, such as diethyl ether or tetrahydrofuran. In general, the reaction is carried out at from 0° to 30° C., preferably at 0° to 20° C. For the reaction, about 1 mole of a complex hydride, such as sodium hydride or lithium alanate, is employed per mole of the ketone of the formula (I). In order to isolate the reduced compound of the formula (I), the residue is taken up in dilute hydrochloric acid and the mixture is then rendered alkaline and extracted with an organic solvent. Further working up is carried out in the customary manner.

If aluminum isopropylate is used, preferred diluents for the reaction according to the invention are alcohols, such as isopropanol, or inert hydrocarbons, such as benzene. The reaction temperatures can again be varied within a substantial range; in general, the reaction is carried out at from 20° to 120° C., preferably at from 50° to 100° C. For carrying out the reaction, about 1 to 2 moles of aluminum isopropylate are employed per mole of the ketone of the formula (I). In order to isolate the reduced compounds of the formula (I), the excess solvent is removed by distillation in vacuo and the aluminum compound formed is decomposed with dilute sulphuric acid or sodium hydroxide solution. Further working up is carried out in the customary manner.

All the physiologically acceptable acids can be used for the preparation of acid addition salts of the compounds of the formula (I). Preferred acids include the hydrogen halide acids (for example hydrobromic acid and especially hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acid (for example p-toluenesulphonic acid and 1,5-naphthalenedisulphonic acid).

The salts of the compounds of the formula (I) can be obtained in a simple manner by conventional salt-formation methods, for example by dissolving a compound of the formula (I) in a suitable inert solvent and adding the acid, for example hydrochloric acid, and can be isolated in a known manner, for example by filtration, and appropriately purified by washing with an inert organic solvent.

Salts which can be used for the preparation of metal salt complexes of the compounds of the formula (I) are preferably salts of metals of main groups II to IV and of sub-groups I and II and IV to VIII, examples of metals which may be mentioned being copper, zinc, manganese, magnesium, tin, iron and nickel. Possible anions of the salts are those which are derived from physiologically acceptable acids, preferably the hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration and appropriately purified by recrystallization.

Examples which may be mentioned of particularly active compounds according to the invention (in addition to those given later in the preparative examples) are (the expression azol-1-yl representing 1,2,4-triazol-1-yl and imidazol-1-yl); 1-(4-chloropyridin-2-yl-oxy)-3,3-dimethyl-1-azol-1-yl-butan-2-one and -ol, 1-(5-chloropyridin-2-yl-oxy)-3,3-dimethyl-1-azol-1-yl-butan-2-one and -ol, 1-(6-bromopyridin-2-yl-oxy)-3,3-dimethyl-1-azol-1-yl-butan-2-one and -ol, 1-(6-fluoropyridin-2-yl-oxy)-3,3-dimethyl-1-azol-1-yl-butan-2-one and -ol, 1-(6-iodopyridin-2-yl-oxy)-3,3-dimethyl-1-azol-1-yl-butan-2-one and -ol, 1-(4-bromopyridin-2-yl-oxy)-3,3-dimethyl-1-azol-1-yl-butan-2-one and -ol, 1-(5-bromopyridin-2-yl-oxy)-3,3-dimethyl-1-azol-1-yl-butan-2-one and -ol, 1-(4,6-dichloropyridin-2-yl-oxy)-3,3-dimethyl-1-azol-1-yl-butan-2-one and -ol, 1-(3,6-dichloropyridin-2-yl-oxy)-3,3-dimethyl-1-azol-1-yl-butan-2-one and -ol, 1-(3,5,6-trichloropyridin-2-yl-oxy)-3,3-dimethyl-1-azol-1-yl-butan-2-one and -ol, 1-(3,6-dibromopyridin-2-yl-oxy)-3,3-dimethyl-1-azol-1-yl-butan-2-one and -ol, 1-(3,5,6-tribromopyridin-2-yl-oxy)-3,3-dimethyl-1-azol-1-yl-butan-2-one and -ol, 1-(4,6-dimethylpyridin-2-yl-oxy)-3,3-dimethyl-1-azol-1-yl-butan-2-one and -ol, 1-(6-trifluoromethylpyridin-2-yl-oxy)-3,3-dimethyl-1-azol-1-yl-butan-2-one and -ol, 1-(4-phenylpyridin-2-yl-oxy)-3,3-dimethyl-1-azol-1-yl-butan-2-one and -ol, 1-(5-phenylpyridin-2-yl-oxy)-3,3-dimethyl-1-azol-1-yl-butan-2-one and -ol, 1-(6-phenylpyridin-2-yl-oxy)-3,3dimethyl-1-azol-1-yl-butan-2-one and -ol, 1-(4-phenoxypyridin-2-yl-oxy)-3,3-dimethyl-1-azol-1-yl-butan-2-one and -ol, 1-(5-phenoxypyridin-2-yl-oxy)-3,3-dimethyl-1-azol-1-yl-butan-2-one and -ol, 1-(6-methoxypyridin-2-yl-oxy)-3,3-dimethyl-1-azol-1-yl-butan-2-one and -ol, 1-(3-cyanopyridin-2-yl-oxy)-3,3-dimethyl-1-azol-1-yl-butan-2-one and -ol, 1-(6-cyanopyridin-2-yl-oxy)-3,3-dimethyl-1-azol-1-yl-butan-2-one and -ol, 1-(2-fluoropyridin-3-yl-oxy)-3,3-dimethyl-1-azol-1-yl-butan-2-one and -ol, 1-(2-iodopyridin-3-yl-oxy)-3,3-dimethyl-1-azol-1-yl-butan-2-one and -ol, 1-(2-methoxypyridin-3-yl-oxy)-3,3-dimethyl-1-azol-1-yl-butan-2-one and -ol, 1-(2-methylpyridin-3-yl-oxy)-3,3-dimethyl-1-azol-1-yl-butan-2-one and -ol, 1-(2-phenylpyridin-3-yl-oxy)-3,3-dimethyl-1-azol-1-yl-butan-2-one and -ol, 1-(2-phenoxypyridin-3-yl-oxy)-3,3-dimethyl-1-azol-1-yl-butan-2-one and -ol, 1-(4-chloropyridin-3-yl-oxy)-3,3-dimethyl-1-azol-1-yl-butan-2-one and -ol, 1-(5-chloropyridin-3-yl-oxy)-3,3-dimethyl-1-azol-1-yl-butan-2-one and -ol, 1-(6-chloropyridin-3-yl-oxy)-3,3-dimethyl-1-azol-1-yl-butan-2-one and -ol, 1-(2,6-dichloropyridin-2-yl-oxy)-3,3-dimethyl-1-azol-1-yl-butan-2-one and -ol, 1-(2,4,6-trichloropyridin-2-yl-oxy)-3,3-dimethyl-1-azol-1-yl-butan-2-one and -ol, 1-(4,5,6-trichloropyridin-2-yl-oxy)-3,3-dimethyl-1-azol-1-yl-butan-2-one and -ol, 1-(2,4,5-trichloropyridin-2-yl-oxy)-3,3-dimethyl-1-azol-1-yl-butan-2-one and -ol, 1-(4-bromopyridin-2-yl-oxy)-3,3-dimethyl-1-azol-1-yl-butan-2-one and -ol, 1-(5-bromopyridin-2-yl-oxy)-3,3-dimethyl-1-azol-1-yl-butan-2-one and -ol, 1-(6-bromopyridin-3-yl-oxy)-3,3-dimethyl-1-azol-1-yl-butan-2-one and -ol, 1-(5-iodopyridin-3-yl-oxy)-3,3-dimethyl-1-azol-1-yl-butan-2-one and -ol, 1-(6-iodopyridin-3-yl-oxy)-3,3-dimethyl-1-azol-1-yl-butan-2-one and -ol, 1-(2,6-dibromopyridin-3-yl-oxy)-3,3-dimethyl-1-azol-1-yl-butan-2-one and -ol, 1-(5-fluoropyridin-3-yl-oxy)-3,3-dimethyl-1-azol-1-yl-butan-2-one and -ol, 1-(6-fluoropyridin-3-yl-oxy)-3,3-dimethyl-1-azol-1-yl-butan-2-one and -ol, 1-(5-phenylpyridin-3-yl-oxy)-3,3-dimethyl-1-azol-1-yl-butan-2-one and -ol, 1-(6-phenylpyridin-3-yl-oxy)-3,3-dimethyl-1-azol-1-yl-butan-2-one and -ol, 1-(4-phenylpyridin-3-yl-oxy)-3,3-dimethyl-1-azol-1-yl-butan-2-one and -ol, 1-(5-phenoxypyridin-3-yl-oxy)-3,3-dimethyl-1-azol-1-yl-butan-2-one and -ol, 1-(6-phenoxypyridin-3-yl-oxy)-3,3-dimethyl-1-azol-1-yl-butan-2-one and -ol, 1-(2-cyanopyridin-3-yl-oxy)-3,3-dimethyl-1-azol-1-yl-butan-2-one and -ol, 1-(2-trifluoromethylpyridin-3-yl-oxy)-3,3-dimethyl-1-azol-1-yl-butan-2-one and -ol, 1-(6-trifluoromethylpyridin-3-yl-oxy)-3,3-dimethyl-1-azol-1-yl-butan-2-one and -ol, 1-(6-methylpyridin-3-yl-oxy)-3,3-dimethyl-1-azol-1-yl-butan-2-one and -ol, 1-(2-chloropyridin-4-yl-oxy)-3,3-dimethyl-1-azol-1-yl-butan-2-one and -ol, 1-(2-bromopyridin-4-yl-oxy)-3,3-dimethyl-1-azol-1-yl-butan-2-one and -ol, 1-(2,6-dichloropyridin-4-yl-oxy)-3,3-dimethyl-1-azol-1-yl-butan-2-one and -ol, 1-(2,6-dibromopyridin-4-yl-oxy)-3,3-dimethyl-1-azol-1-yl-butan-2-one and -ol, 1-(2-phenylpyridin-4-yl-oxy)-3,3-dimethyl-1-azol-1-yl-butan-2-one and -ol, 1-(2,6-dimethylpyridin-4-yl-oxy)-3,3-dimethyl-1-azol-1-yl-butan-2-one and -ol, 1-(2,6-difluoropyridin-4-yl-oxy)-3,3-dimethyl-1-azol-1-yl-butan-2-one and -ol, and 1-(2-fluoropyridin-4-yl-oxy)-3,3-dimethyl-1-azol-1-yl-butan-2-one and -ol.

The active compounds according to the invention exhibit a powerful fungitoxic action. They do not damage crop plants in the concentrations required for combating fungi. For these reasons they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which infect above-ground parts of plants or attack the plants through the soil, as well as against seed-borne pathogens. They develop a particularly good activity against parasitic fungi on above-ground parts of plants.

As plant protection agents, the active compounds according to the invention can be used with particularly good success for combating powdery mildew fungi, for example for combating powdery mildew of cucumbers (*Erysiphe cichoriacearum*), powdery mildew of cereals as well as against other cereal diseases, such as cereal rust and stripe disease of barley; they can also be used for combating species of Venturia, for example against the apple scab causative organism (*Fusicladium dendriticum*), and the fungi Pyricularia and Pellicularia. It should be particularly emphasized that the active compounds according to the invention not only develop a protective action, but in some cases also have a curative action, that is to say when used after infection has taken place. The systemic action of some of the substances should also be emphasized. Thus, it is possible to protect plants against fungal attack when the active compound is fed to the above-ground parts of the plant via the soil and the root or via the seed.

As plant protection agents, the active compounds according to the invention can be used for the treatment of seed or soil and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

The formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellents, such as halogenated hydrocarbons as well as butane, propane, nitrogen and carbon dioxide.

As solid carriers they may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkylsulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a substantial range. They are, in general, from 0.1 to 0.00001 percent by weight, preferably from 0.05 to 0.0001 percent.

In the treatment of seed, amounts of active compound of generally 0.001 to 50 g, preferably 0.01 to 10 g, are employed per kilogram of seed.

For the treatment of soil, amounts of active compound of generally 1 to 1000 g, especially 10 to 200 g, are employed per cubic meter of soil.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The following examples illustrate the preparation of the novel compounds of the invention:

EXAMPLE 1

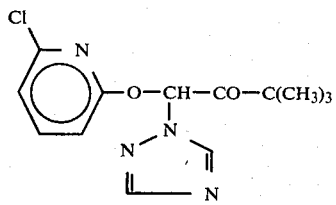

a (Process variant a)

(I) Preparation of the precursor

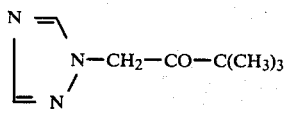

13.45 g (1 mol) of 1-chloro-3,3-dimethyl-butan-2-one, 69 g (1 mol) of 1,2,4-triazole and 140 g (1 mol) of powdered potassium carbonate were heated under reflux in 500 ml of acetone for 6 hours, while stirring. Thereafter, the mixture was allowed to cool, the inorganic salt was filtered off and the filtrate was concentrated in vacuo. After treatment with diisopropyl ether, the oily residue crystallized out. After drying, 123.6 g (74% of theory) of 3,3-dimethyl-1-(1,2,4-triazol-1-yl)-butan-2-one of melting point 63°–65° C. were obtained.

(II) Preparation of the starting material

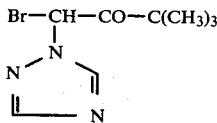

80 g (0.5 mol) of bromine were slowly added dropwise to 83.5 g (0.5 mol) of 3,3dimethyl-1-(1,2,4-triazol-1-yl)-butan-2-one and 41 g (0.5 mol) of anhydrous sodium acetate in 250 ml of glacial acetic acid at 40° to 50° C., while stirring. The mixture was further stirred at 40° C. until it was completely decolorized. Thereafter, the reaction mixture was discharged onto 400 ml of water and extracted three times with 100 ml of chloroform each time. The combined organic phases were washed first with sodium bicarbonate solution until the evolution of $CO_2$ had ended, and then with water, and were dried over sodium sulphate and concentrated in vacuo by distilling off the solvent. Crude 1-bromo-3,3-dimethyl-1-(1,2,4-triazol-1-yl)-butan-2-one, which was further reacted directly, was obtained quantitatively.

(III) 50.5 g (0.5 mol) of triethylamine were added dropwise to 123 g (0.5 mol) of crude 1-bromo-3,3-dimethyl-1-(1,2,4-triazol-1-yl)-butan-2-one and 65 g (0.5 mol) of 6-chloro-2-hydroxy-pyridine in 250 ml of absolute acetonitrile at 24° to 30° C., while stirring. The mixture was stirred at room temperature for 3 hours and filtered and the filtrate was concentrated in vacuo. After treatment with water, the residue crystallized out. 76.6 g (52% of theory) of 1-(6-chloropyridin-2-yl-oxy)-3,3-dimethyl-1-(1,2,4-triazol-1-yl)-butan-2-one of melting point 103°–105° C. were obtained.

b (Process variant b)

(I) Preparation of the precursor

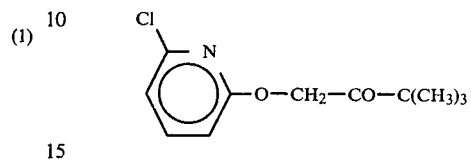

27 g (0.2 mol) of monochloropinacolin, 26 g (0.2 mol) of 6-chloro-2-hydroxy-pyridine and 28 g (0.2 mol) of powdered potassium carbonate were heated under reflux in 150 ml of acetone for 3 hours, while stirring. Thereafter, the mixture was allowed to cool, the salt which had precipitated was filtered off and the filtrate was concentrated in vacuo. The oily residue was taken up in petroleum ether, the solution was cooled to $-10°$ C. and the crystalline precipitate which thereby separated out was filtered off and dried. 24.5 g (54% of theory) of 1-(6-chloropyridin-2-yl-oxy)-3,3-dimethyl-butan-2-one were obtained.

(II) Preparation of the starting material

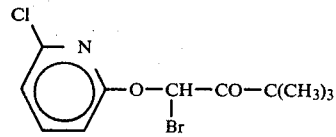

22.7 g (0.1 mol) of 1-(6-chloropyridin-2-yl-oxy)-3,3-dimethyl-butan-2-one and 8.2 g (0.1 mol) of anhydrous sodium acetate were suspended in 100 ml of galcial acetic acid, and 16 g (0.1 mol) of bromine were slowly added at 40° to 50° C. The mixture was further stirred at 40° C. until it was completely decolorized. Thereafter, the reaction mixture was discharged onto 200 ml of water and extracted twice with 100 ml of chloroform each time. The combined organic phases were washed first with sodium bicarbonate solution until the evolution of $CO_2$ had ended, and then with water, and were dried over sodium sulphate and concentrated in vacuo by distilling off the solvent. Crude 1-bromo-1-(6-chloropyridin-2-yl-oxy)-3,3-dimethyl-butan-2-one, which was further reacted directly, was obtained quantitatively.

(III) 39.5 g (0.1 mol) of crude 1-bromo-1-(6-chloropyidin-2-yl-oxy)-3,3-dimethyl-butan-2-one in 100 ml of acetonitrile were slowly added to a solution of 6.9 g (0.1 mol) of 1,2,4-triazole and 10.1 g (0.1 mol) of triethylamine in 100 ml of acetonitrile at 20° C. Thereafter, the mixture was stirred under reflux for 1 hour and concentrated by distilling off the solvent and the residue was taken up in water and thereby crystallized. After recrystallizing from ethyl acetate/petroleum ether, 13.5 g (45% of theory) of 1-(6-chloropyridin-2-yl-oxy)-3,3-dimethyl-1-(1,2,4-triazol-1-yl)-butan-2-one of melting point 105° C. were obtained.

c (Process variant c)

33.8 g (0.2 mol) of 1,1-dichloro-3,3-dimethyl-butan-2-one, 26 g (0.2 mol) of 6-chloro-2-hydroxy-pyridine, 21 g (0.3 mol) of 1,2,4-triazole and 56 g (0.4 mol) of potassium carbonate were heated under reflux in 250 ml of acetone for 12 hours, while stirring. Thereafter, the mixture was allowed to cool, the salt which had precipitated was filtered off and the filtrate was concentrated in vacuo. Isopropanol was added to the oily residue, it being possible to isolate successively three crystal fractions. The first two contained mainly 1,1-bis-(1,2,4-triazol-1-yl)-3,3-dimethylbutan-2-one of melting point 157°–158° C. and 1,1-bis-(6-chloropyridin-2-yl-oxy)-3,3-dimethyl-butan-2-one of melting point 102°–104° C. 4 g of 1-(6-chloropyridin-2-yl-oxy)-3,3-dimethyl-1-(1,2,4-triazol-1-yl)-butan-2-one of melting point 102° C. were obtained from the third fraction.

EXAMPLE 2

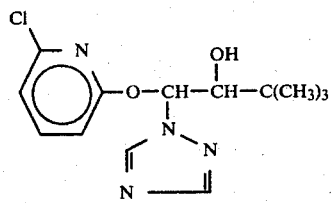
(2)

Reduction 11.8 g (0.04 mol) of 1-(6-chloropyridin-2-yl-oxy)-3,3-dimethyl-1-(1,2,4-triazol-1-yl)-butan-2-one (Example 1) were dissolved in 100 ml of methanol, and 1.8 g (0.04 mol) of sodium borohydride were added in portions at 20°–30° C., while stirring. After the exothermic reaction had ended, 5 ml of concentrated hydrochloric acid were added dropwise and the mixture was stirred at room temperature for 1 hour. Thereafter, 200 ml of water were added and the mixture was neutralised with sodium bicarbonate solution. The reaction mixture was extracted by shaking with ether and the organic phase was dried over sodium sulphate and concentrated. 5.3 g (54% of theory) of 1-(6-chloropyridin-2-yl-oxy)-3,3-dimethyl-1-(1,2,4-triazol-1-yl)butan-2-ol were obtained as a viscous oil in the form of a diastereomer mixture.

EXAMPLE 3

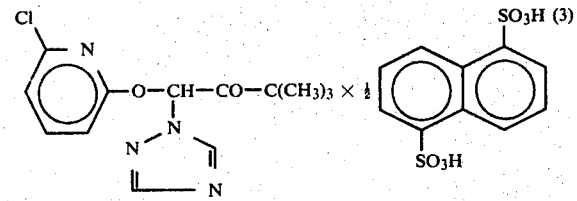
(3)

Salt Formation 10 g (0.034 mol) of 1-(6-chloropyridin-2-yl-oxy)-3,3-dimethyl-1-(1,2,4-triazol-1-yl)-butan-2-one (Example 1) were dissolved in 50 ml of acetone, and a solution of 8 g (0.027 mol) of naphthalene-1,5-disulphonic acid in 50 ml of acetone was added. The salt which precipitated after some time was filtered off and dried. 14 g (94% of theory) of 1-(6-chloropyridin-2-yl-oxy)-3,3-dimethyl-1-(1,2,4-triazol-1-yl)-butan-2-one naphthalene-1,5-disulphonate of melting point 212°–215° C. (decomposition) were obtained.

The compounds listed in the table which follows were obtained analogously.

TABLE I

R'—O—CH—X—R
      |
      N
     ╱ ╲
    N   A
    ‖   ‖
    N———

| Compound No | A | R | R' | X | Melting point (°C.) |
|---|---|---|---|---|---|
| 4 | N | C(CH$_3$)$_3$ | Cl—pyridin-2-yl | CHOH | 202–04(D.) (× ½ NDS) |
| 5 | N | C(CH$_3$)$_3$ | Cl—pyridin-2-yl | CO | 164 |
| 6 | CH | C(CH$_3$)$_3$ | Cl—pyridin-2-yl | CO | 214–18(D.) (× ½ NDS) |
| 7 | CH | C(CH$_3$)$_3$ | Cl—pyridin-2-yl | CO | viscous oil |
| 8 | CH | C(CH$_3$)$_3$ | Cl—pyridin-2-yl | CO | 195–200 (D.) (× ½ NDS) |
| 9 | N | C(CH$_3$)$_3$ | Br—pyridin-2-yl | CO | 81–83 |
| 10 | CH | C(CH$_3$)$_3$ | Br—pyridin-2-yl | CO | viscous oil |
| 11 | CH | C(CH$_3$)$_3$ | Cl—pyridin-2-yl | CO | 79–82 |
| 12 | CH | C(CH$_3$)$_3$ | Cl—pyridin-2-yl | CHOH | amorphous |

TABLE I-continued

R'—O—CH—X—R
with N-A / N ring (imidazole-like)

| Compound No | A | R | R' | X | Melting point (°C.) |
|---|---|---|---|---|---|
| 13 | N | C(CH₃)₃ | 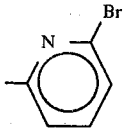 Br, N-phenyl | CO | 92–95 |
| 14 | N | C(CH₃)₃ | 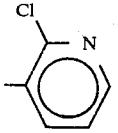 Cl, N-phenyl | CO | crystal mass |
| 15 | N | C(CH₃)₃ | 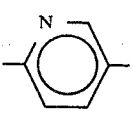 N-phenyl-I | CO | 140 |

The fungicidal activity of the compounds of this invention is illustrated by the following examples:

EXAMPLE 4

Erysiphe test (cucumbers)/systemic

Solvent: 4.7 parts by weight of acetone
Emulsifier: 0.3 part by weight of alkylaryl polyglycol ether
Water: 95.0 parts by weight The amount of active compound required to give the desired concentration of active compound in the watering liquid was mixed with the stated amount of solvent and the concentrate was diluted with the stated amount of water which contained the stated amount of emulsifier.

Cucumber plants grown in standard soil, in the 1 to 2 leaf stage, were watered three times within one week with 10 ml of the watering liquid, of the desired concentration of active compound, per 100 ml of soil.

The plants treated in this way were inoculated, after treatment, with conidia of the fungus *Erysiphe cichoriacearum*. The plants were then set up in a greenhouse at 23° to 24° C. and 70 percent relative humidity. After 12 days, the infection of the cucumber plants was determined.

In this test, for example, compounds 1 and 6 showed a very good action which was distinctly superior to that of the compounds known from the prior art.

EXAMPLE 5

Fusicladium test (apple)/protective

Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4 to 6 leaf stage were sprayed with the spray liquid until dripping wet. The plants remained in a greenhouse for 24 hours at 20° C. and at a relative atmospheric humidity of 70 percent. They were then inoculated with an aqueous conidium suspension of the apple scab causative organism (*Fusicladium dendriticum*) and incubated for 18 hours in a humidity chamber at 18° to 20° C. and at a relative atmospheric humidity of 100 percent.

The plants were then brought into a greenhouse again for 14 days.

15 days after inoculation, the infection of the seedlings was determined. In this test compounds 1 and 6 showed a very good action which was distinctly superior to that of the compounds known from the prior art.

EXAMPLE 6

Shoot treatment test/powdery mildew of cereal/protective/curative (leaf-destructive mycosis)

To produce a suitable preparation of active compound, 0.25 part by weight of active compound was taken up in 25 parts by weight of dimethylformamide and 0.06 part by weight of alkylaryl polyglycol ether and then 975 parts by weigh of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

To test for curative activity the corresponding procedure was followed in converse sequence. The treatment of the single-leaved young barley plants with the preparation of active compound was carried out 48 hours after inoculation, when the infection was already manifest.

After 6 days' dwell time of the plants at a temperature of 21°–22° C. and 80–90 percent relative humidity the occurrence of mildew pustules on the plants was evaluated. The more active the compound, the lower the degree of mildew infection.

In this test compounds 1, 3 and 6 showed a very good action which was distinctly superior to that of the compounds known from the prior art.

EXAMPLE 7

Powdery mildew of barley test (*Erysiphe graminis* var. *hordei*)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their fast leaf, they were dusted with fresh spores of *Erysiphe graminis* var. *hordei* and grown on at 21°–22°

C. and 80–90 percent relative atmospheric humidity and 16 hours' exposure to light. The typical mildew pustules formed on the leaves over the course of 6 days. The more active the compound, the lower the degree of mildew infection.

In this test compound 6 showed a very good action which was distinctly superior to that of the compounds known from the prior art.

EXAMPLE 8

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether, and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1 percent strength aqueous agar. After the spore suspension had dried on, the wheat plants were sprayed with the preparation of active compound until dew-moist and were placed, for incubation, in a greenhouse for 24 hours at about 20° C. and 100 percent relative humidity.

After 10 days' dwell time of the plants at a temperature of 20° C. and 80–90 percent relative humidity, the occurrence of rust pustules on the plant was evaluated. The more active the compound, the lower was the degree of rust infection.

In this test compound 6 showed a very good action which was distinctly superior to that of the compounds known from the prior art.

EXAMPLE 9

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Drechslera graminea* (commonly described as *Helminthosporium gramineum*), was shaken with the dressing in a closed glass flask. The seed, on moist filter paper discs in closed Petri dishes, was exposed to a temperature of 4° C. for 10 days in a refrigerator. The germination of the barley, and possibly also of the fungus spores, was thereby initiated. 2 batches of 50 grains of the pregerminated barley were subsequently sown 2 cm deep in Fruhstorfer standard soil and cultivated in a greenhouse at temperatures of about 18° C. in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

In this test compounds 1 and 6 showed a very good action which was distinctly superior to that of the compounds known from the prior art.

EXAMPLE 10

Pyricularia and Pellicularia test

Solvent: 11.75 parts by weight of acetone
Dispersing agent: 0.75 part by weight of alkylaryl polyglycol ether
Water: 987.50 parts by weight The amount of active compound required for the desired concentration of active compound in the spray liquor was mixed with the stated amount of the solvent and of the dispersing agent, and the concentrate was diluted with the stated amount of water.

Rice plants about 2–4 weeks old were sprayed with the spray liquor until dripping wet. The plants remained in a greenhouse at temperatures of 22° to 24° C. and a relative atmospheric humidity of about 70 percent until they were dry. Thereafter, some of the plants were inoculated with an aqueous suspension of 100,000 to 200,000 spores/ml of *Pyricularia oryzae* and placed in a chamber at 24° to 26° C. and 100 percent relative atmospheric humidity. The other plants were infected with a culture of *Pellicularia sasakii* grown on malt agar and were set up at 28° to 30° C. and 100 percent relative atmospheric humidity.

5 to 8 days after the inoculation, the infection of all the leaves present at the time of inoculation with *Pyricularia oryzae* was determined as a percentage of the untreated but also inoculated control plants. In the case of the plants infected with *Pellicularia sasakii*, the infection at the leaf sheaths after the same time was determined, again in relation to the untreated but infected control.

In this test compounds 3 and 6 showed a very good action which was distinctly superior to that of the compounds known from the prior art.

It will be appreciated that the instant specification and examples are set forth by way of illustration and not limitation, and that various modifications and changes may be made without departing from the spirit and scope of the present invention.

What is claimed is:

1. 1-(6-chloropyridin-2-yl-oxy)-3,3-dimethyl-1-(1,2,4-triazol-1-yl)-butan-2-ol of the formula

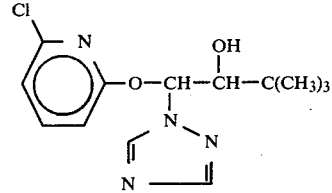

2. A fungicidal composition containing as active ingredient a fungicidally effective amount of a compound according to claim 1 in admixture with an inert diluent.

3. A method of combating fungi which comprises applying to said fungi, or to a habitat thereof, a fungicidally effective amount of a compound according to claim 1.

* * * * *

UNITED STATES PATENT AND TRADEMARK OFFICE
CERTIFICATE OF CORRECTION

PATENT NO. : 4,396,624
DATED : Aug. 2, 1983
INVENTOR(S) : Jörg Stetter et al

It is certified that error appears in the above—identified patent and that said Letters Patent is hereby corrected as shown below:

Column 14, line 55, Insert --NDS = 1,5-naphthalenedisulphonic acid D = melts with decomposition--.

Signed and Sealed this

First Day of November 1983

[SEAL]

Attest:

GERALD J. MOSSINGHOFF

Attesting Officer  Commissioner of Patents and Trademarks